United States Patent
Brooks

(10) Patent No.: US 8,632,604 B2
(45) Date of Patent: Jan. 21, 2014

(54) MEDICAL IMPLANT DEVICE

(75) Inventor: James Brooks, Leeds (GB)

(73) Assignee: Depuy International Limited (GB)

( * ) Notice: Subject to any disclaimer, the term of this patent is extended or adjusted under 35 U.S.C. 154(b) by 33 days.

(21) Appl. No.: 13/503,052

(22) PCT Filed: Oct. 20, 2010

(86) PCT No.: PCT/EP2010/065786
§ 371 (c)(1),
(2), (4) Date: Jun. 21, 2012

(87) PCT Pub. No.: WO2011/048138
PCT Pub. Date: Apr. 28, 2011

(65) Prior Publication Data
US 2012/0253468 A1 Oct. 4, 2012

(30) Foreign Application Priority Data
Oct. 22, 2009 (GB) .................................. 0918484.7

(51) Int. Cl.
*A61F 2/28* (2006.01)
(52) U.S. Cl.
USPC ........................................................ 623/23.5
(58) Field of Classification Search
USPC ............ 623/23.5–23.61, 23.72–23.76, 23.36, 623/23.29, 22.33, 22.32, 22.31, 18.11, 623/16.11, 17.11–17.16; 427/2.1, 427/2.24–2.27, 212, 216, 217, 256
See application file for complete search history.

(56) References Cited

U.S. PATENT DOCUMENTS

| 3,707,006 | A | * | 12/1972 | Bokros et al. | 424/422 |
| 3,808,606 | A | * | 5/1974 | Tronzo | 428/613 |
| 3,840,904 | A | * | 10/1974 | Tronzo | 623/22.32 |
| 3,855,638 | A | * | 12/1974 | Pilliar | 623/23.55 |
| 4,202,055 | A | * | 5/1980 | Reiner et al. | 623/23.57 |
| 4,272,855 | A | * | 6/1981 | Frey | 623/16.11 |
| 4,355,428 | A | * | 10/1982 | Deloison et al. | 623/23.5 |
| 4,361,630 | A | * | 11/1982 | Johnson, Sr. | 428/613 |
| 4,542,539 | A | * | 9/1985 | Rowe et al. | 623/23.57 |
| 4,550,448 | A | * | 11/1985 | Kenna | 623/23.6 |
| 4,589,883 | A | * | 5/1986 | Kenna | 623/23.35 |
| 4,673,409 | A | * | 6/1987 | Van Kampen | 623/23.29 |
| 4,713,076 | A | * | 12/1987 | Draenert | 623/23.6 |

(Continued)

FOREIGN PATENT DOCUMENTS

| EP | 1035230 A1 | 9/2000 |
| EP | 1997524 A1 | 12/2008 |
| WO | WO 9316656 A2 | 9/1993 |

OTHER PUBLICATIONS

PCT International Search Report and Written Opinion PCT/EP2010/065786 dated Jan. 3, 2011.

(Continued)

*Primary Examiner* — Alvin Stewart

(57) ABSTRACT

A medical implant device comprises a substrate (10) having an undulating surface provided by peaks (12) which are separated by recesses (14). The device includes a porous coating layer provided on the undulating surface of the substrate which comprises a plurality of particles (16). The spacing between adjacent peaks on the surface of the substrate is less than the particle size of the particles. The particles are bonded to the peaks on the surface of the substrate and adjacent particles are bonded to one another.

14 Claims, 2 Drawing Sheets

(56) References Cited

U.S. PATENT DOCUMENTS

| | | | | |
|---|---|---|---|---|
| 4,737,411 A * | 4/1988 | Graves et al. | 428/403 |
| 4,743,262 A * | 5/1988 | Tronzo | 623/22.32 |
| 4,769,041 A * | 9/1988 | Morscher | 623/22.37 |
| 4,828,563 A * | 5/1989 | Muller-Lierheim | 623/23.63 |
| 4,834,756 A * | 5/1989 | Kenna | 128/898 |
| 4,846,393 A * | 7/1989 | Devillard | 228/178 |
| 4,865,603 A * | 9/1989 | Noiles | 623/23.5 |
| 4,883,491 A * | 11/1989 | Mallory et al. | 623/22.31 |
| 4,911,720 A * | 3/1990 | Collier | 623/23.12 |
| 4,955,909 A * | 9/1990 | Ersek et al. | 623/23.74 |
| 5,002,572 A * | 3/1991 | Picha | 623/23.74 |
| 5,002,575 A * | 3/1991 | Johnson | 623/23.5 |
| 5,007,931 A * | 4/1991 | Smith | 623/23.3 |
| 5,156,625 A * | 10/1992 | Marchetti et al. | 623/22.33 |
| 5,178,201 A * | 1/1993 | Ahlers | 164/34 |
| 5,246,530 A * | 9/1993 | Bugle et al. | 216/56 |
| 5,258,030 A * | 11/1993 | Wolfarth et al. | 623/23.55 |
| 5,263,986 A * | 11/1993 | Noiles et al. | 623/23.55 |
| 5,405,389 A * | 4/1995 | Conta et al. | 623/23.55 |
| 5,433,750 A * | 7/1995 | Gradinger et al. | 623/23.54 |
| 5,441,537 A * | 8/1995 | Kenna | 419/2 |
| 5,443,510 A * | 8/1995 | Shetty et al. | 419/2 |
| 5,489,306 A * | 2/1996 | Gorski | 623/23.55 |
| 5,507,815 A * | 4/1996 | Wagner et al. | 623/23.5 |
| 5,549,691 A * | 8/1996 | Harwin | 623/22.37 |
| 5,645,593 A * | 7/1997 | Woods et al. | 623/23.5 |
| 5,676,700 A * | 10/1997 | Black et al. | 623/23.28 |
| 5,702,473 A * | 12/1997 | Albrektsson et al. | 623/22.31 |
| 5,728,510 A * | 3/1998 | White | 430/323 |
| 5,734,959 A | 3/1998 | Krebs | |
| 5,746,272 A * | 5/1998 | Mastrorio et al. | 164/516 |
| 5,766,263 A * | 6/1998 | Grundei et al. | 623/23.15 |
| 6,008,432 A * | 12/1999 | Taylor | 623/23.3 |
| 6,106,558 A * | 8/2000 | Picha | 623/23.74 |
| 6,120,544 A * | 9/2000 | Grundei et al. | 623/23.14 |
| 6,146,425 A * | 11/2000 | Hoermansdoerfer | 623/22.31 |
| 6,149,689 A * | 11/2000 | Grundei | 623/23.5 |
| 6,193,762 B1 * | 2/2001 | Wagner et al. | 623/66.1 |
| 6,206,924 B1 * | 3/2001 | Timm | 623/17.16 |
| 6,231,612 B1 * | 5/2001 | Balay et al. | 623/22.31 |
| 6,293,971 B1 * | 9/2001 | Nelson et al. | 623/23.63 |
| 6,299,647 B1 * | 10/2001 | Townley | 623/22.32 |
| 6,312,473 B1 * | 11/2001 | Oshida | 623/23.55 |
| 6,319,285 B1 * | 11/2001 | Chamier et al. | 623/22.32 |
| 6,485,521 B1 * | 11/2002 | Say et al. | 623/23.55 |
| 6,491,723 B1 * | 12/2002 | Beaty | 623/11.11 |
| 6,554,867 B1 * | 4/2003 | Joos | 623/23.5 |
| 6,558,422 B1 * | 5/2003 | Baker et al. | 623/16.11 |
| 6,572,654 B1 * | 6/2003 | Santilli | 623/17.16 |
| 6,599,322 B1 * | 7/2003 | Amrich et al. | 623/23.5 |
| 6,620,200 B1 * | 9/2003 | Descamps et al. | 623/22.32 |
| 6,638,311 B2 * | 10/2003 | Wang et al. | 623/22.32 |
| 6,641,616 B1 * | 11/2003 | Grundei | 623/23.26 |
| 6,733,503 B2 * | 5/2004 | Layrolle et al. | 606/77 |
| 6,811,569 B1 * | 11/2004 | Afriat et al. | 623/22.32 |
| 6,911,048 B2 * | 6/2005 | Fernandez et al. | 623/23.18 |
| 6,948,350 B2 * | 9/2005 | Ono et al. | 72/329 |
| 6,949,124 B2 * | 9/2005 | Serbousek et al. | 623/23.31 |
| 7,048,870 B1 * | 5/2006 | Ellingsen et al. | 216/109 |
| 7,051,417 B2 * | 5/2006 | Michelson | 29/557 |
| 7,169,185 B2 * | 1/2007 | Sidebotham | 623/22.21 |
| 7,214,246 B2 * | 5/2007 | Serbousek et al. | 623/23.31 |
| 7,241,316 B2 * | 7/2007 | Evans et al. | 623/23.51 |
| 7,244,275 B2 * | 7/2007 | Michelson | 623/23.5 |
| 7,258,810 B2 * | 8/2007 | Hunter et al. | 216/41 |
| 7,323,013 B2 * | 1/2008 | McTighe et al. | 623/23.5 |
| 7,341,757 B2 * | 3/2008 | Yadav | 427/2.14 |
| 7,368,065 B2 * | 5/2008 | Yang et al. | 216/83 |
| 7,497,876 B2 * | 3/2009 | Tuke et al. | 623/23.5 |
| 7,550,091 B2 * | 6/2009 | Beaty | 216/109 |
| 7,575,603 B2 * | 8/2009 | Bergin et al. | 623/23.31 |
| 7,767,250 B2 * | 8/2010 | Luan et al. | 427/2.1 |
| 7,771,485 B2 * | 8/2010 | Grundei | 623/23.11 |
| 7,771,773 B2 * | 8/2010 | Namavar | 427/2.1 |
| 7,771,774 B2 * | 8/2010 | Berckmans et al. | 427/2.1 |
| 7,776,097 B2 * | 8/2010 | Tepic et al. | 623/22.24 |
| 7,842,096 B2 * | 11/2010 | Fridshtand et al. | 623/23.35 |
| 7,875,083 B2 * | 1/2011 | Sudmann | 623/23.29 |
| 7,892,290 B2 * | 2/2011 | Bergin et al. | 623/23.46 |
| 7,931,683 B2 * | 4/2011 | Weber et al. | 623/1.42 |
| 7,947,084 B2 * | 5/2011 | Link | 623/23.26 |
| 7,988,733 B2 * | 8/2011 | Shimp et al. | 623/17.11 |
| 8,043,375 B2 * | 10/2011 | Strzepa et al. | 623/14.12 |
| 8,066,770 B2 * | 11/2011 | Rivard et al. | 623/16.11 |
| 8,128,706 B2 * | 3/2012 | Kaigler, Sr. | 623/23.57 |
| 8,206,454 B2 * | 6/2012 | Hormansdorfer | 623/22.31 |
| 8,206,455 B2 * | 6/2012 | Fridshtand et al. | 623/23.35 |
| 8,257,435 B2 * | 9/2012 | Pitkin et al. | 623/15.12 |
| 8,317,870 B2 * | 11/2012 | Wagner et al. | 623/20.32 |
| 8,343,229 B2 * | 1/2013 | Coale | 623/23.5 |
| 8,361,161 B2 * | 1/2013 | Buma et al. | 623/22.11 |
| 8,372,423 B2 * | 2/2013 | Marshall et al. | 424/423 |
| 8,383,187 B2 * | 2/2013 | Rivard et al. | 427/2.26 |
| 8,506,642 B1 * | 8/2013 | Lyren | 623/22.11 |
| 2001/0056303 A1 * | 12/2001 | Caneiro et al. | 623/23.74 |
| 2002/0111691 A1 * | 8/2002 | Wang et al. | 623/22.32 |
| 2003/0055511 A1 * | 3/2003 | Schryver et al. | 623/23.5 |
| 2004/0186586 A1 * | 9/2004 | Seyer et al. | 623/22.12 |
| 2004/0243247 A1 * | 12/2004 | Kuoni et al. | 623/22.32 |
| 2005/0038521 A1 * | 2/2005 | Hoermansdoerfer | 623/22.31 |
| 2005/0267585 A1 * | 12/2005 | Sidebotham | 623/22.28 |
| 2007/0150068 A1 * | 6/2007 | Dong et al. | 623/22.32 |
| 2008/0039950 A1 * | 2/2008 | Splieth et al. | 623/22.12 |
| 2008/0208353 A1 * | 8/2008 | Kumar et al. | 623/23.56 |
| 2008/0243113 A1 * | 10/2008 | Shastri et al. | 606/33 |
| 2008/0306607 A1 * | 12/2008 | Hakamatsuka et al. | 623/23.5 |
| 2009/0105842 A1 * | 4/2009 | Noetzli et al. | 623/23.35 |
| 2009/0187256 A1 * | 7/2009 | Rauguth et al. | 623/23.55 |
| 2009/0292367 A1 * | 11/2009 | Borden | 623/23.75 |
| 2009/0317766 A1 * | 12/2009 | Heidenau et al. | 433/201.1 |
| 2010/0057197 A1 * | 3/2010 | Weber et al. | 623/1.42 |
| 2010/0057219 A1 * | 3/2010 | Lee | 623/23.76 |
| 2010/0318193 A1 * | 12/2010 | Desai et al. | 623/23.76 |
| 2011/0022160 A1 * | 1/2011 | Flanagan et al. | 623/1.42 |
| 2011/0218643 A1 * | 9/2011 | Yerokhin | 623/23.6 |
| 2011/0264231 A1 * | 10/2011 | Theillez et al. | 623/22.32 |
| 2012/0095568 A1 * | 4/2012 | Grappiolo | 623/23.26 |
| 2012/0253468 A1 * | 10/2012 | Brooks | 623/23.5 |
| 2013/0110255 A1 * | 5/2013 | Picha et al. | 623/23.74 |
| 2013/0236502 A1 * | 9/2013 | Marshall et al. | 424/400 |

OTHER PUBLICATIONS

UK Search Report GB0918484.7—date of search Feb. 5, 2010.

* cited by examiner

MEDICAL IMPLANT DEVICE

CROSS REFERENCE TO RELATED APPLICATION

This application is a National Stage 35 U.S.C. 371 of International Patent Application PCT/EP2010/065786 filed Oct. 20, 2010.

BACKGROUND OF THE INVENTION

This invention relates to a medical implant device having a porous surface for tissue ingrowth.

Medical implant devices can be anchored at an implant site by ingrowth of tissue into a porous surface region of the implant. For example, U.S. Pat. No. 3,855,638 discloses a component of an orthopaedic joint prosthesis which comprises a metal substrate having a porous metal coating into which bone tissue can grow. The coating is provided by metal particles which are jointed to each other and to the substrate to define a plurality of connected, interstitial pores which are distributed throughout the coating. The coating is formed by a sintering process.

BRIEF SUMMARY OF THE INVENTION

EP-A-1997524 discloses a component of an orthopaedic joint prosthesis in which a substrate has a porous surface region provided by two layers of metal particles which are bonded to one another and to the surface of the substrate by a sintering process. The inner layer comprises spherical particles and the outer surface comprises aspherical particles. The layer of aspherical particles results in increased roughness of the surface of the component, compared with a component whose surface is provided by spherical particles. The porosity of a surface layer provided by aspherical particles can increase progressively towards the surface of the component, and the porosity of the layer can be greater at the surface than the porosity of a layer which is formed from spherical particles with similar size. It is therefore possible to accommodate greater ingrowth of bone tissue, which provides for stronger fixation of the component when implanted.

U.S. Pat. No. 5,443,510 discloses an implant in which a porous surface region is created by sintering beads on to a mesh which is welded to the implant surface. This is said to reduce notch formation at sinter sites on the substrate surface of a device in which beads are sintered directly on to the surface. The mesh increases the thickness of the surface region of the implant. The security of the fixation of the implant depends in part on the fixation of the mesh to the substrate surface.

The present invention provides an implant device which has an undulating surface provided by peaks which are separated by recesses, with particles bonded to the undulating surface which are bigger than the gaps between the peaks.

Accordingly, in one aspect, the invention provides a medical implant device, which comprises a substrate having an undulating surface provided by peaks which are separated by recesses, in which the device includes a porous coating layer provided on the undulating surface of the substrate which comprises a plurality of particles, in which the spacing between adjacent peaks on the surface of the substrate is less than the particle size of the particles, and in which particles are bonded to the peaks on the surface of the substrate and adjacent particles are bonded to one another.

In another aspect, the invention provides a method of making a medical implant device, which comprises:

a. forming a substrate having an undulating surface provided by peaks which are separated by recesses,
b. applying a layer of particles on the said surface of the substrate, in which the spacing between adjacent peaks on the surface of the substrate is less than the particle size of the particles, and
c. bonding (i) particles to the peaks on the surface of the substrate and (ii) adjacent particles to one another.

The particles and the shapes of the peaks and the recesses between them should be such that the particles cannot fit into the recesses to contact the surface of the substrate at the bases of the recesses. Bonds between the particles and the substrate surface are therefore formed on the peaks (on the tops of the peaks or on the sides of the peaks), spaced apart from the base of the recesses.

The implant of the present invention has the advantage that the tendency for notches to initiate and to propagate through the substrate is reduced because the particles are bonded to the peaks on the substrate surface. In the event that a notch starts to form in a peak at the interface between the peak and a particle, the notch can propagate through the peak as far as an adjacent recess. Further propagation can then be inhibited, in particular through the bulk of the implant substrate.

Preferably, the surfaces of a particle and the top or side of a peak to which the particle is bonded are both convex. When the bond is formed by sintering, the extent of deformation of the surface of the substrate can be reduced compared with the surface of a substrate which is essentially planar (without an array of peaks and recesses). It is believed that this reduced deformation of the surface can help to reduce the initiation of notches in the substrate.

The device of the invention is believed to have an increased resistance to fatigue failure by virtue of the provision of peaks and recesses on the surface of the substrate.

In particular, the implant of the invention can have the advantage of improved fatigue strength compared with a device in which the substrate does not have the peaks and recesses feature of the present invention.

Preferably, the peaks are spaced apart regularly on the surface of the substrate. This can facilitate manufacture of the substrate. It can help to ensure that particles whose size is within an appropriately controlled range contact the peaks on the substrate surface and do not sit in the recesses between the peaks.

The peaks can comprise ridges in which the length of each ridge is greater than its width, and in which the recesses comprise troughs between the ridges. For example, the substrate surface can be provided by a plurality of approximately uniformly spaced ridges having troughs between them. A plurality of uniformly spaced ridges having troughs between them can be formed as a helical thread.

The recesses can comprise troughs in which at least some of the peaks, preferably all of the peaks, are surrounded by troughs when viewed in plan from above the surface. The peaks can be rounded, for example circular, at least at the top of the peaks, when viewed from above the surface. The peaks can have several sides. For example the peaks might have at least four sides. The peaks can have four sides when the troughs are straight and are in two intersecting arrays with the angle between two arrays of troughs is 90°. The peaks will be square when the distances between the troughs of the first array is equal to the distance between the troughs of the second array. The peaks might have three sides when the troughs are straight and are in three intersecting arrays, for example with the angle between the troughs of the arrays being 60°.

Preferably, the base of a recess between adjacent peaks is rounded when viewed in cross-section. This can help to reduce the tendency for cracks to form at the bases of the recesses. Preferably, the portions of the bases of the recesses that are rounded have an approximately constant radius. The constant radius portions of the bases of the recesses can extend through an angle of arc of at least about 45°, preferably at least about 60°, more preferably at least about 80°, especially at least about 100°, for example at least about 120° or at least about 130°. Preferably, the constant radius portions of the bases of the recesses extend through an angle of arc of not more than about 175°, for example not more than about 160° or not more than about 150°.

Preferably, the relationship between of the transverse dimension of the particles (which will be their diameter when they are spherical) and the radius of the recesses is such that the particles cannot fit into the recesses to contact the surface of the substrate at the bases of the recesses.

Preferably, the peaks are rounded when viewed in cross-section. This can help to reduce the tendency for any cracks to initiate at the interface between a peak and a particle which is bonded to it. Preferably, the portions of the peaks that are rounded have an approximately constant radius. The constant radius portions of the bases of the recesses can extend through an angle of arc of at least about 45°, preferably at least about 60°, more preferably at least about 80°, especially at least about 100°, for example at least about 120° or at least about 130°. Preferably, the constant radius portions of the peaks extend through an angle of arc of not more than about 175°, for example not more than about 160° or not more than about 150°.

Preferably the ratio of the radius which defines the base of a recess which is rounded to the radius which defines an adjacent peak which is rounded is at least about 0.7, more preferably at least about 0.8, especially at least about 0.9. Preferably the said ratio is not more than about 1.3, more preferably not more than about 1.2, especially not more than about 1.1.

Preferably the ratio of the distance between adjacent recesses which are rounded to the radius which defines the base of the recesses is at least about 2.5, more preferably at least about 3.5. The value of the ratio will generally be not more than about 6, preferably not more than about 5.

Preferably the ratio of the distance between adjacent peaks which are rounded to the radius which defines the peaks is at least about 2.5, more preferably at least about 3.5. The value of the ratio will generally be not more than about 6, preferably not more than about 5.

Preferably the ratio of the height of two peaks which are rounded, measured from the base of the recess between them, to the radius which defines the peaks is at least about 1.0, more preferably at least about 1.2. Preferably, the value of the ratio is not more than about 2.0, more preferably not more than about 1.6, for example not more than about 1.4.

Preferably, the ratio of the radius of the peaks to the size of the particles which are bonded to the peaks is not more than about 0.7, more preferably not more than about 0.6. Preferably, the ratio of the radius of the peaks to the size of the particles which are bonded to the peaks is at least about 0.3, more preferably at least about 0.4.

Preferably the ratio of the height of the peaks, measured from the base of the recess between them which is rounded, to the radius which defines the recess is at least about 1.0, more preferably at least about 1.2. Preferably, the value of the ratio is not more than about 2.0, more preferably not more than about 1.6, for example not more than about 1.4.

Preferably, the particles which are bonded to the peaks on the surface of the substrate have a generally rounded shape so that they do not have any edges or corners. Preferably, the particles which are bonded to the peaks on the surface of the substrate are approximately spherical so that, prior to any changes in shape resulting from the process of bonding them to the substrate, the surface of any one of particles is defined by an approximately constant radius (meaning that the longest chord measured across the particle varies by not more than 10%).

The sizes of the particles which are used in the device of the invention can be measured using mesh sieves. Particles which are applied to the surface of the substrate can have a single mode particle size distribution or a multimode (for example bimodal) particle size distribution. The device can have applied to it a first layer of particles which have a first size distribution and a second layer of particles which has a second size distribution.

Preferably the particle size of the particles which are bonded to the peaks on the surface of the substrate is at least about 50 µm, more preferably at least about 80 µm, especially at least about 120 µm, for example at least about 150 µm. The size of the spherical particles will generally be not more than about 400 µm, preferably not more than about 325 µm, more preferably not more than about 275 µm, for example not more than about 250 µm. There will generally be a spread of particle sizes; it will generally be preferred that at least 85% by weight of the particles meet these size limitations.

Preferably, the distance between two adjacent peaks on the surface of the substrate is at least about 50 µm, more preferably at least about 80 µm, especially at least about 120 µm, for example at least about 150 µm. Preferably, the distance between two adjacent peaks is not more than about 400 µm, more preferably not more than about 320 µm, especially not more than about 270 µm, for example not more than about 240 µm.

Preferably, the size profile of the particles which are bonded to the surface of the substrate is such that they are able to pack together in an approximately close packed array. This is facilitated by minimising the spread of the sizes of the particles. Preferably, the peaks on the surface of the substrate are able to fit in to the close packed array of particles which are bonded to it so that the layer of the particles which is in immediate contact with the surface is approximately close packed.

Preferably the ratio of the particle size of the particles which are bonded to the peaks on the surface of the substrate to the distance between two closest adjacent peaks is at least about 0.8, more preferably at least about 0.9. Preferably the ratio of the particle size of the particles which are bonded to the peaks on the surface of the substrate to the distance between two closest adjacent peaks is not more than about 1.2, more preferably not more than about 1.1, for example about 1.0.

Preferably, the device includes a cover layer which overlies the coating layer and which is provided by a plurality of cover layer particles, in which the cover layer particles are bonded to the particles of the coating layer and adjacent particles of the cover layer are bonded to one another, and in which the particles of the coating layer are approximately spherical and the particles of the cover layer are aspherical.

The aspherical particles can be rounded in shape. Preferably, the shape of the aspherical particles is angular so that it is defined by corners and/or edges and/or recesses. The size of aspherical particles can be established using mesh sieves so that the measured particle size is defined by the size of the apertures in a sieve through which the particles can pass. One or more layers of aspherical particles can be applied on top of one or more layers of particles which are spherical.

Preferably, the particles on the surface of the substrate are provided in one or more layers which have a total thickness, measured from the top of the peaks on the substrate surface, of at least about 250 µm, more preferably at least about 300 µm, especially at least about 500 µm. The thickness can be at least about 800 µm or at least about 1000 µm. The thickness of the layers of particles on the surface of the substrate will normally be not more than about 2000 µm.

The surface of the substrate, at least towards the surface on which the particles are provided, will generally be provided by a metal. The particles will generally be formed from a metal. It will generally be preferred that the material of the substrate, at least at its surface, is substantially the same as the material of the particles. Metals which might be used in the implant device include titanium and its alloys (such as, for example, Ti-6Al-4V), tantalum and its alloys, stainless steels such as are commonly used in the manufacture of implant devices, and alloys of cobalt and chromium (optionally with other elements such as for example molybdenum). When the surface of the substrate and the particles are both provided by a metal, it can be preferred to bond the particles to the substrate and to each other by a sintering process. The particles can be suspended in a slurry in an aqueous solution which contains an organic binder such as, for example, methyl cellulose. The slurry can be held in a mould, surrounding the portion of the surface of the substrate which is to have the particles applied to it. The slurry is heated to remove the water. The particles and the substrate are then exposed to heat in an inert or reducing atmosphere to burn off the binder and to fuse the particles to one another and to the substrate.

A suitable sintering process can involve:

Ensuring that the substrate surface is clean and smooth.
Applying a coating of organic binder to the substrate surface.
Submerging the substrate in a fluidised bed of metal particles for 2 to 3 seconds while agitated.
Applying an overspray coating of binder.
Repeating the submersion and overspray steps.
Removing any high spots; filling any low spots.
Repeating the coating, submersion and overspray steps as necessary to build up a sufficient thickness of particles.
Placing the coated product in an oven.

An implant device in which the substrate is formed from titanium and the particles are formed from titanium can be sintered adequately at a temperature of about 1250° C. The length of the period in which the device is exposed to elevated temperature will depend on the mass of the substrate. The period must be sufficiently long for the particles to be fixed securely to the substrate. By way of example, in the case of the acetabular shell component of a hip joint prosthesis, a heating time of from 100 to about 300 minutes will generally be appropriate. Longer times can be appropriate for articles in which the substrate has a greater thermal mass.

The technique which is used to create the peaks and recesses features will depend on the shape and arrangement of the features on the surface of the substrate. It will generally be preferred that the features are formed by a machining process. The creation of recesses which are in the form of relatively long troughs which separate adjacent peaks can be facilitated by forming them as a continuous helical thread. Relatively long troughs, whether in the form of discrete circular features or a continuous helical thread, can be created on the surface of a substrate having a circular cross-section using a lathe. Peaks and recesses features can be formed on substrates having other shapes and in other forms using different techniques such as etching techniques, for example acid etching or laser etching or a combination of the two.

The bone facing surface of the implant device can be treated to promote desirable interactions with bone tissue, for example to encourage ingrowth of bone tissue. For example, the surface of the device can be coated with a hydroxy apatite material.

BRIEF DESCRIPTION OF THE DRAWINGS

Embodiments of the invention are described below by way of example with reference to the accompanying drawings, in which.

DETAILED DESCRIPTION OF THE INVENTION

Figure 1:
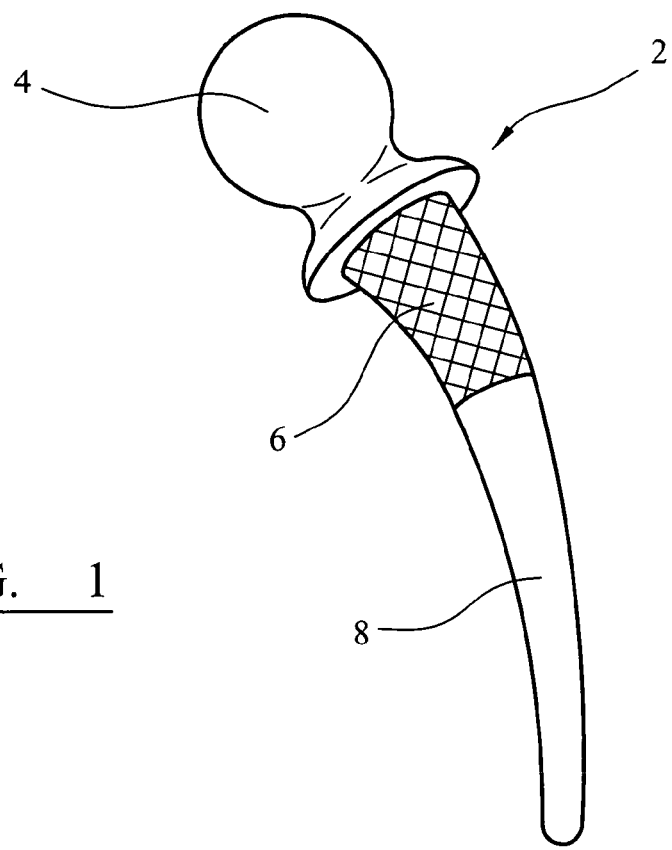
FIG. 1 is a side view of a femoral component of a hip joint prosthesis, which includes particles bonded to the surface of a substrate.

FIG. 1 shows a femoral component of a hip joint prosthesis which includes a stem 2 which can be fitted into the prepared intramedullary cavity in the femur, and a head 4 which can articulate in the hollow acetabular component of the prosthesis. The stem has a proximal epiphyseal portion 6 and a distal portion 8. The stem is formed from titanium to a conventional shape and using techniques which are well known from the manufacture of orthopaedic joint prostheses.

The epiphyseal portion 6 of the stem 4 includes a layer of titanium particles which have been bonded to the surface of the stem substrate by means of a sintering process.

While FIG. 1 shows the application of the invention to the femoral component of a hip joint prosthesis, the invention can be applied to the bone facing surface of other implant components where it is intended that bone tissue should bond to the surface of the components by ingrowth of bone tissue, including for example the acetabular component of a hip joint prosthesis, the femoral component of a knee joint prosthesis, the tibial component of a knee joint prosthesis, the humeral component of a shoulder joint prosthesis, the glenoid component of a shoulder joint prosthesis, components of elbow and ankle joint prostheses, components such as pins, nails, and rods (including intramedullary pins, nails and rods) and plates such as might be used in the treatment of fractures, and components for implantation in a patient's spine such as rods, plates etc.

Figure 2:
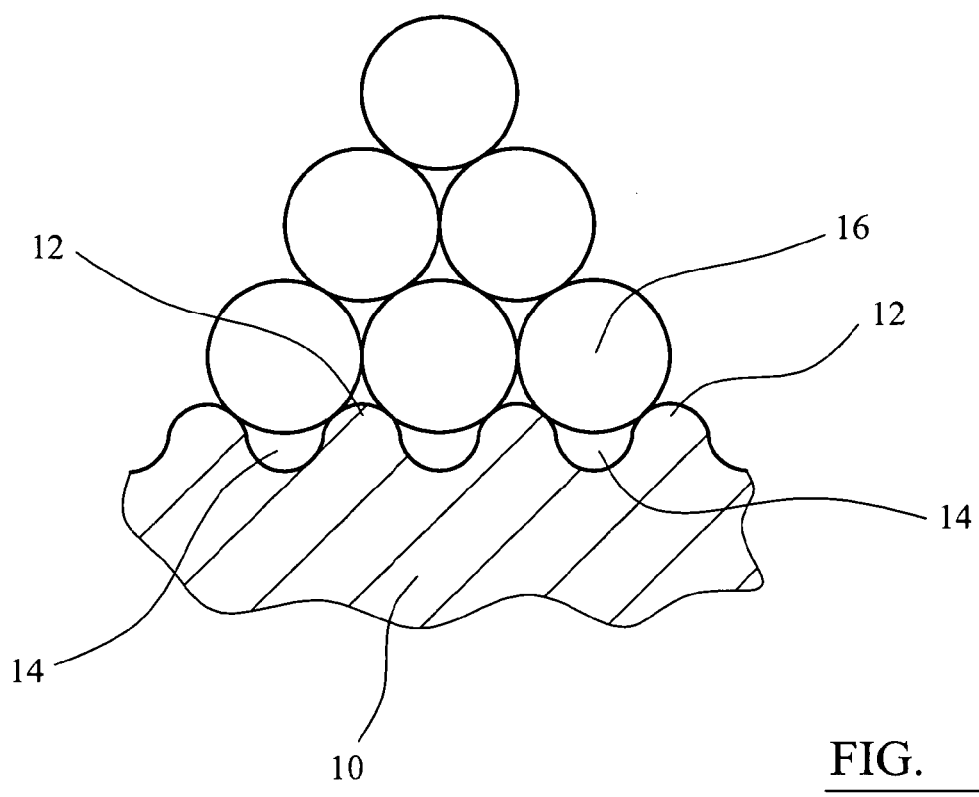
FIG. 2 is a schematic cross-sectional view of the surface region of the femoral component shown in FIG. 1.

FIG. 2 shows the stem substrate 10 which has a helical groove formed on its surface which defines a plurality of peaks 12, separated by grooves 14. The top of each peak is rounded with a radius of 50 µm. The bottom of each groove is rounded with a radius of 50 µm. The spacing between two adjacent grooves is 200 µm. The depth of each groove is 80 µm.

The titanium particles 16 which are bonded to the surface of the epiphyseal portion of the stem substrate are spherical with a radius of about 100 µm. The particles are sized so that sit against the rounded surfaces of the peaks 12 and so that they cannot fit into the grooves 14 between the peaks 12 to contact the bases of the grooves. Successive layers of particles can form close packed array with the particles which sit against the rounded surfaces of the peaks. It should be appreciated that the arrangement of the particles on the surface of the substrate as shown in FIG. 2 is schematic. It might be that peaks on the surface of a substrate might not have particles bonded to them. It will be understood however that the size of the particles and the shapes of the peaks and the recesses between them are such that the particles cannot fit into the recesses to contact the surface of the substrate at the bases of the recesses.

The implant device can have a cover layer of aspherical particles applied to the spherical particles 16, for example as disclosed in EP-A-1997524.

Figure 3:
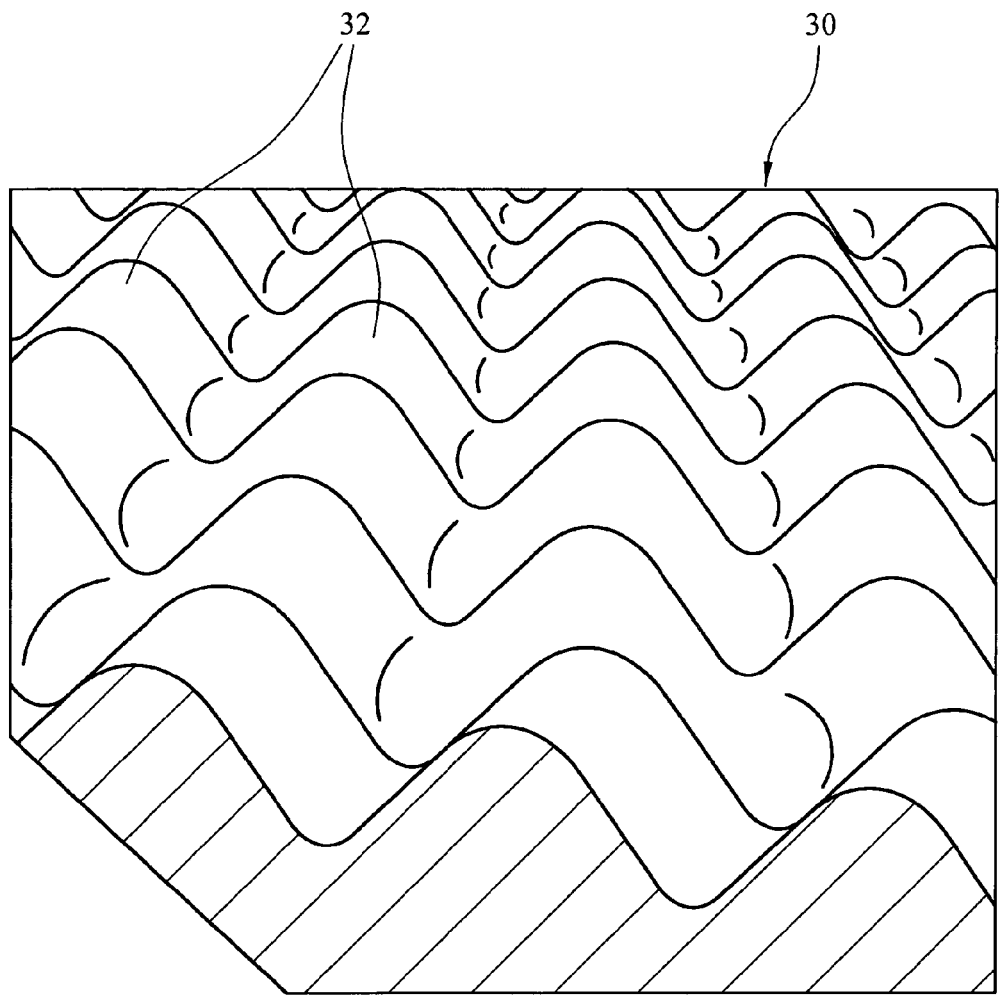
FIG. 3 is an isometric view of the surface of a substrate whose surface is provided by a plurality of peaks which are separated by troughs, in which each peaks is surrounded by the troughs.

FIG. 3 shows a substrate 30 whose surface is provided by a plurality of peaks 32. Each peak is surrounded by a recess in the form of a trough. The depth of the troughs in the embodiment shown in FIG. 3 varies around the periphery of the peaks. However it is envisaged that the depth of the troughs might be approximately constant around the peaks. Particles can be bonded to the surface of the substrate 30 so that they contact one or more of the peaks. Appropriately sized particles will sit against the rounded surfaces of the peaks and so that they cannot fit into the troughs between the peaks to contact the bases of the troughs. The particles will generally be sized so that they contact a square array of four peaks.

The invention claimed is:

1. A medical implant device, comprising a substrate having an undulating surface provided by peaks that are separated by recesses, wherein the device includes a porous coating layer provided on the undulating surface of the substrate and the porous coating layer includes a plurality of particles, wherein the spacing between adjacent peaks on the surface of the substrate is less than the particle size of the particles, and wherein particles are bonded to at least some of the peaks on the surface of the substrate and adjacent particles are bonded to one another.

2. The device of claim 1, wherein the peaks are spaced apart regularly on the surface of the substrate.

3. The device of claim 1, wherein the peaks comprise ridges, each ridge having a width and a length, the length being greater than the width, and wherein the recesses comprise troughs.

4. The device of claim 1, wherein the recesses comprise troughs and wherein the peaks are surrounded by the troughs.

5. The device of claim 1, wherein the surface of the substrate is provided by a metal and wherein the particles are formed from a metal.

6. The device of claim 5, wherein the particles are bonded to the peaks on the surface of the substrate and to one another by means of a sintering process.

7. The device of claim 1, wherein the particles have an approximately spherical shape.

8. The device of claim 1, wherein at least some of the recesses have a base and wherein the bases between adjacent peaks are rounded.

9. The device of claim 8, wherein the portions of the bases of the recesses that are rounded have an approximately constant radius.

10. The device of claim 1, wherein the peaks are rounded.

11. The device of claim 10, wherein the portions of the peaks that are rounded have an approximately constant radius.

12. The device of claim 11, wherein the ratio of the radius of the peaks to the size of the particles that are bonded to the peaks is not more than about 0.7.

13. The device of claim 1, further comprising a cover layer that overlies the porous coating layer and which includes a plurality of cover layer particles, wherein the cover layer particles are bonded to the particles of the coating layer and adjacent particles of the cover layer are bonded to one another, and wherein the particles of the coating layer are approximately spherical and the particles of the cover layer are aspherical.

14. A method of making a medical implant device, comprising:
   a. forming a substrate having an undulating surface provided by peaks which are separated by recesses,
   b. applying a layer of particles on the said surface of the substrate, wherein the spacing between adjacent peaks on the surface of the substrate is less than the particle size of the particles, and
   c. bonding (i) particles to the peaks on the surface of the substrate and (ii) adjacent particles to one another.

* * * * *